United States Patent
Baumgardner et al.

[11] Patent Number: 5,976,123
[45] Date of Patent: Nov. 2, 1999

[54] HEART STABILIZATION

[75] Inventors: Jonathan M. Baumgardner; David R. Hennings, both of Auburn; Bruce J. Sand, Calabasas; Gerald Elsbach, Auburn, all of Calif.

[73] Assignee: Laser Aesthetics, Inc., Auburn, Calif.

[21] Appl. No.: 08/938,923

[22] Filed: Sep. 26, 1997

Related U.S. Application Data

[63] Continuation-in-part of application No. 08/692,929, Jul. 30, 1996, Pat. No. 5,820,626.

[51] Int. Cl.$^6$ .................................................... A61B 17/38
[52] U.S. Cl. .................................................. 606/13
[58] Field of Search ..................... 606/9, 10, 11, 606/12, 13, 14, 15, 16, 17, 27, 28, 29, 30, 31, 32, 33, 34, 41, 46, 20, 21, 22

[56] References Cited

U.S. PATENT DOCUMENTS

| | | | |
|---|---|---|---|
| 3,630,203 | 12/1971 | Sellinger et al. | 606/20 |
| 3,821,510 | 6/1974 | Muncheryan | 606/14 |
| 4,376,376 | 3/1983 | Gregory | 62/51 |
| 4,860,744 | 8/1989 | Johnson et al. | 606/21 |
| 5,020,995 | 6/1991 | Levy | 606/15 |
| 5,098,428 | 3/1992 | Sandlin et al. | 606/22 |
| 5,344,418 | 9/1994 | Ghaffari | 606/9 |

OTHER PUBLICATIONS

Selective cooling of biological tissues: application for thermally mediated procedures Arvari et al, Phys. Med. Biol. 40 (1995) 241–252.

*Primary Examiner*—John P. Leubecker
*Assistant Examiner*—Sonya Harris-Ogugua
*Attorney, Agent, or Firm*—Ray K. Shahani, Esq.

[57] ABSTRACT

A cooling handpiece and method for use in therapeutic, cosmetic or aesthetic, diagnostic, exploratory, interventional or other medical procedures, the handpiece for use in conjunction with a controllable energy source such as coherent light, non-coherent light or laser light, ultrasound energy, radio frequency energy and other types of electromagnetic and mechanical energy, the handpiece comprising a main body portion adapted for directing the energy to target tissue, the main body portion further adapted for receiving a removable reservoir containing coolant fluid, the reservoir having an attachment means for releasable attachment of the reservoir to the handpiece, and the handpiece having a controllable valve for delivery of a portion of the coolant fluid to the target tissue.

44 Claims, 8 Drawing Sheets

HEART STABILIZATION

RELATED APPLICATIONS

This is a continuation-in-part of U.S. patent application Ser. No. 08/692,929 filed Jul. 30, 1996, now U.S. Pat. No. 5,820,626.

FIELD OF THE INVENTION

This invention relates to cryogenic cooling in conjunction with laser or other energy delivery devices, including laser, radio frequency, ultrasound and other sonic energy, electromagnetic, chemical, mechanical and other types of energy, for use in medical and other applications, and more particularly, to a handpiece with a removable coolant fluid reservoir for use in surgical, aesthetic, dermatology, intervention, diagnostic and other medical methods and techniques utilizing flushing and/or cooling.

BACKGROUND AND ADVANTAGES OF THE INVENTION

In medical and other types of laser applications, laser delivery handpieces are widely used. With the development of optical fibers and solid-state lasers, complex arrangements of collimating lenses, mirrors and filters have been replaced with small, efficient laser delivery devices utilizing fiber optics.

U.S. Pat. No. 5,020,995 issued Jun. 4, 1991 to Levy teaches a surgical treatment and method for cutting tooth tissue. A handpiece for cutting dentin and enamel is disclosed which contains a hollow tube connected to an external source of cooling fluid. The apparatus has a number of drawbacks, however, including the need for peripheral tubing and other connections to control and laser source. In practice, these plurality of external connections make the device awkward to use. Furthermore, if the coolant source is located farther than about 0.5 to about 1.0 meter from the outlet end positioned to direct coolant onto the tissue being cooled, either significant insulation is required or a considerable purge time will be necessary to deliver coolant fluid at a low temperature to the desired location on demand.

U.S. Pat. No. 5,344,418 issued Sep. 6, 1994 to Ghaffari teaches an optical system for treatment of vascular lesions. In addition to the drawbacks noted above, principally the need for external connections and complicated piping, insulation and purging requirements, the cooling system in intended to cool the sapphire lens of the system. The patent also refers to a system for the control of skin temperature.

Recently, a great deal of attention has been given to selective cooling of biological tissue during thermally mediated therapeutic procedures. B. Anvari et al., *Selective Cooling of Biological Tissues: Application for Thermally Mediated Therapeutic Procedures,* Phys. Med. Biol. 40 (1995) 241–252. Methods and systems have been proposed based on models of heat conduction in various types of tissue at various levels beneath the skin. In certain dermatological applications the objective has been to produce a photo and/or thermal effect primarily to subsurface tissue, without destroying or altering superficial structures. Examples of such procedures include laser treatment of port wine stains and the clinical treatment of other dermatoses, lesions and tattoos. Experiments have been performed that use, for example, infrared radiometry to measure the thermal response of in vivo human skin to cooling by a cryogen spurt.

While a information has been gained from these studies and others about the effect of such cooling on biological tissue during such operations, very little effective or efficient equipment is commercially available. Often, applying spurts of cryogenic materials to a site of laser delivery results in splashing of the cryogenic liquid and/or unconfined and uncontrollable cooling.

Therefore, it is an advantage of the present invention to provide an improved handpiece for performing thermally mediated medical, therapeutic, cosmetic and other procedures with selective cooling of surface tissue.

It is a further advantage of the present invention to provide a light, unrestricted handpiece for such procedures.

It is a further advantage of the present invention to provide an apparatus with an on-board cryogen or other coolant fluid reservoir.

It is a further advantage of the present invention to provide such apparatus which allows visualization of the remaining amount of coolant fluid and which is refillable.

It is a further advantage of the present invention to provide such apparatus in which both coolant and laser energy are both delivered in a controlled, confined manner to avoid delivery of both laser energy and coolant to undesired locations.

It is a further advantage of the present invention to provide such apparatus with a refillable cryogen fluid reservoir.

It is a further advantage of the present invention to provide such apparatus with a removable cryogen fluid reservoir.

It is a further advantage of the present invention to provide a handpiece for delivering energy such as from a laser or other therapeutic device to target tissue, the handpiece having an on-board cooling system comprising individual disposable or re-usable cylinders or cartridges of cryogen or other cooling fluid which couple to the handpiece and can be replaced conveniently and efficiently as needed.

It is a further advantage of the present invention to provide a handpiece with coolant for delivering energy, including laser, radio frequency, ultrasound and other sonic energy, electromagnetic, chemical, mechanical and other types of energy.

It is a further advantage of the present invention to provide methods of using such apparatus, in medical and aesthetic procedures including but not limited in any way to wrinkle removal, hair removal, tattoo removal, port-wine and other pigmentation adjustment, etc.

It is a further advantage of the present invention to provide apparatus and methods for reformation of collagen.

SUMMARY OF THE INVENTION

The invention is a handpiece for use in therapeutic procedures employing selective cooling. The apparatus is intended for use in conjunction with a controllable laser source or other type of energy delivery device, including radio frequency devices, ultrasound devices, etc. The apparatus comprises a handpiece portion for physically manipulating and controlling the apparatus, an energy delivery means for controllably delivering a predetermined amount of energy to a preselected surface area, coolant reservoir means having a predetermined volume, cryogen fluid contained in the reservoir means, releasable attachment means for securely and releasably coupling the reservoir to a valve means, the valve means for controllably delivering a portion of the cryogen fluid to the preselected surface area.

A preferred embodiment comprises delivery tube means having a proximal and a distal end, the laser delivery means and the valve means coupled to the delivery tube such that both the laser energy and the portion of the predetermined volume of cryogen are controllably delivered to the preselected surface area. In a preferred embodiment, the reservoir comprises a transparent tube, thus providing a visual indication of the volume or cryogen fluid remaining in the reservoir. In a preferred embodiment, the valve means comprises a controllable solenoid valve. A preferred embodiment, comprises a laser delivery means focusing means.

The present invention is an improved method and device for reformation of collagen. In a preferred embodiment, collagen connective tissue in skin can be contracted or shrunk instantaneously, thus tightening the overlying tissue without the superficial damage or destruction associated with other techniques of superficial skin resurfacing. In another preferred embodiment, the method and device is highly beneficial in therapeutic contraction of the collagen connective tissue within the musculo-skeletal system. Superficial heat exchange by means of a dynamic cooling process enhance these modalities by eliminating pain or discomfort and reducing any risk of superficial destruction of the skin tissue.

The present invention is a method for reformation of collagen tissue comprising the step of irradiating the tissue with laser energy having a wavelength in the range of about 1 to about 12 microns. In a preferred embodiment, the temperature of the collagen is raised to between about 58 and about 62 degrees Celsius. In a preferred embodiment, the energy has a wavelength in the range of about 1.2 to about 1.8 microns. In a preferred embodiment, the energy has a wavelength of about 1.3–1.4 microns. In a preferred embodiment, the energy is delivered in a continuous wave. In a preferred embodiment, the energy is delivered in a pulsed mode. In a preferred embodiment, the pulse rate of delivery of the laser energy is such that the pulses of energy are delivered within the thermal relaxation time period for the given volume of tissue being thermally treated. In a preferred embodiment, the total energy delivered is in the range of about 4 to about 50 joules per square centimeter.

Skin which is subjected to long-term sun exposure exhibits a variety of clinical changes which have been attributed to aging. The major histopathological finding in photoaging is the accumulation of material in the papillary dermis which has staining characteristics similar to elastin and, therefore, the condition is termed "solar elastosis".

Solar elastosis replaces the normal collagen in the papillary dermis which results in the clinical changes observed in photoaged skin such as wrinkles. Increased collagen degradation occurs from the UV exposure which has been shown to stimulate collagenase production by human fibroblasts and to upregulate collagenase gene expression.

Collagen production, however, remains unchanged in this condition. The net result is, therefore, a relative decrease in the steady-state collagen levels in photoaged skin, predominately in the papillary dermis.

Although there is no established histological finding which directly correlates with the appearance of wrinkling in photodamaged skin, it has been accepted that a net reduction in collagen levels is the etiologic component. This is based upon the hypothesis that collagen provides the cutaneous strength and resiliency.

In addition to these anatomical factors, clinical improvement in wrinkles has been histologically correlated with collagen synthesis in various cutaneous treatment modalities. These include chemical cutaneous peels, dermabrasion, use of topical tretinoin and laser assisted skin resurfacing.

The mechanism of wrinkle reduction is, therefore, based upon the reversal of the net collagen reduction stimulated by solar exposure. The net gain of collagen in the papillary dermis results from a biological response to iatrogenic injury, whether by chemical, mechanical or laser-induced trauma. The biological response is in the form of the complex sequence of events incorporated in the wound repair process culminating in, among other factors, histological, immunohistological and in situ hybridization evidence of new collagen synthesis in the papillary dermis.

The present invention is, therefore, a method for the reduction of the fine wrinkles which result from photodamage to the skin.

Since the superficial skin layer, the epidermis, plays no role in the reduction of wrinkles by the reformation of collagen in the papillary dermal layer of the skin, there would be a distinct advantage gained by protecting this outer layer during the process of inciting a wound healing response in the dermal layer.

It is an advantage of the present invention, therefore, to provide a controllable dynamic cooling process to prevent said epidermal damage by means of the disclosed handpiece with coolant reservoir. Skin which is subjected to long-term sun exposure exhibits a variety of clinical changes which have been attributed to aging. The major histopathological finding in photoaging is the accumulation of material in the papillary dermis which has staining characteristics similar to elastin and, therefore, the condition is termed "solar elastosis".

Solar elastosis replaces the normal collagen in the papillary dermis which results in the clinical changes observed in photoaged skin such as wrinkles. Increased collagen degradation occurs from the UV exposure which has been shown to stimulate collagenase production by human fibroblasts and to upregulate collagenase gene expression.

Collagen production, however, remains unchanged in this condition. The net result is, therefore, a relative decrease in the steady-state collagen levels in photoaged skin, predominately in the papillary dermis.

Although there is no established histological finding which directly correlates with the appearance of wrinkling in photodamaged skin, it has been accepted that a net reduction in collagen levels is the etiologic component. This is based upon the hypothesis that collagen provides the cutaneous strength and resiliency.

In addition to these anatomical factors, clinical improvement in wrinkles has been histologically correlated with collagen synthesis in various cutaneous treatment modalities. These include chemical cutaneous peels, dermabrasion, use of topical tretinoin and laser assisted skin resurfacing.

The mechanism of wrinkle reduction is, therefore, based upon the reversal of the net collagen reduction stimulated by solar exposure. The net gain of collagen in the papillary dermis results from a biological response to iatrogenic injury, whether by chemical, mechanical or laser-induced trauma. The biological response is in the form of the complex sequence of events incorporated in the wound repair process culminating in, among other factors, histological, immunohistological and in situ hybridization evidence of new collagen synthesis in the papillary dermis.

The present invention is, therefore, a method for the reduction of the fine wrinkles which result from photodamage to the skin.

Since the superficial skin layer, the epidermis, plays no role in the reduction of wrinkles by the reformation of collagen in the papillary dermal layer of the skin, there would be a distinct advantage gained by protecting this outer layer during the process of inciting a wound healing response in the dermal layer.

It is an advantage of the present invention, therefore, to provide a controllable dynamic cooling process to prevent said epidermal damage by means of the disclosed handpiece with coolant reservoir.

Numerous other advantages and features of the present invention will become readily apparent from the following detailed description of the invention and the embodiments thereof, from the claims and from the accompanying drawings in which the details of the invention are fully and completely disclosed as a part of this specification.

DETAILED DESCRIPTION OF THE INVENTION

The feasibility of selectively cooling biological tissues has been explored experimentally. Infrared radiometry can be used to measure the thermal response of in vivo human skin to cooling by a cryogen spurt. One model assumes a two-layered semi-infinite medium consisting of skin in contact with a cold film whose thickness may change with time. The term "boundary layer" refers to a film of cryogenic material in contact with both air and skin. When cryogen is spurted onto the skin surface, skin temperature is reduced as a result of supplying the latent heat of vaporization. As the skin surface temperature approaches the boiling point of the cryogen, the rate at which cryogen droplets evaporate becomes less than the accumulation rate or cryogen on the surface.

Figure 1:
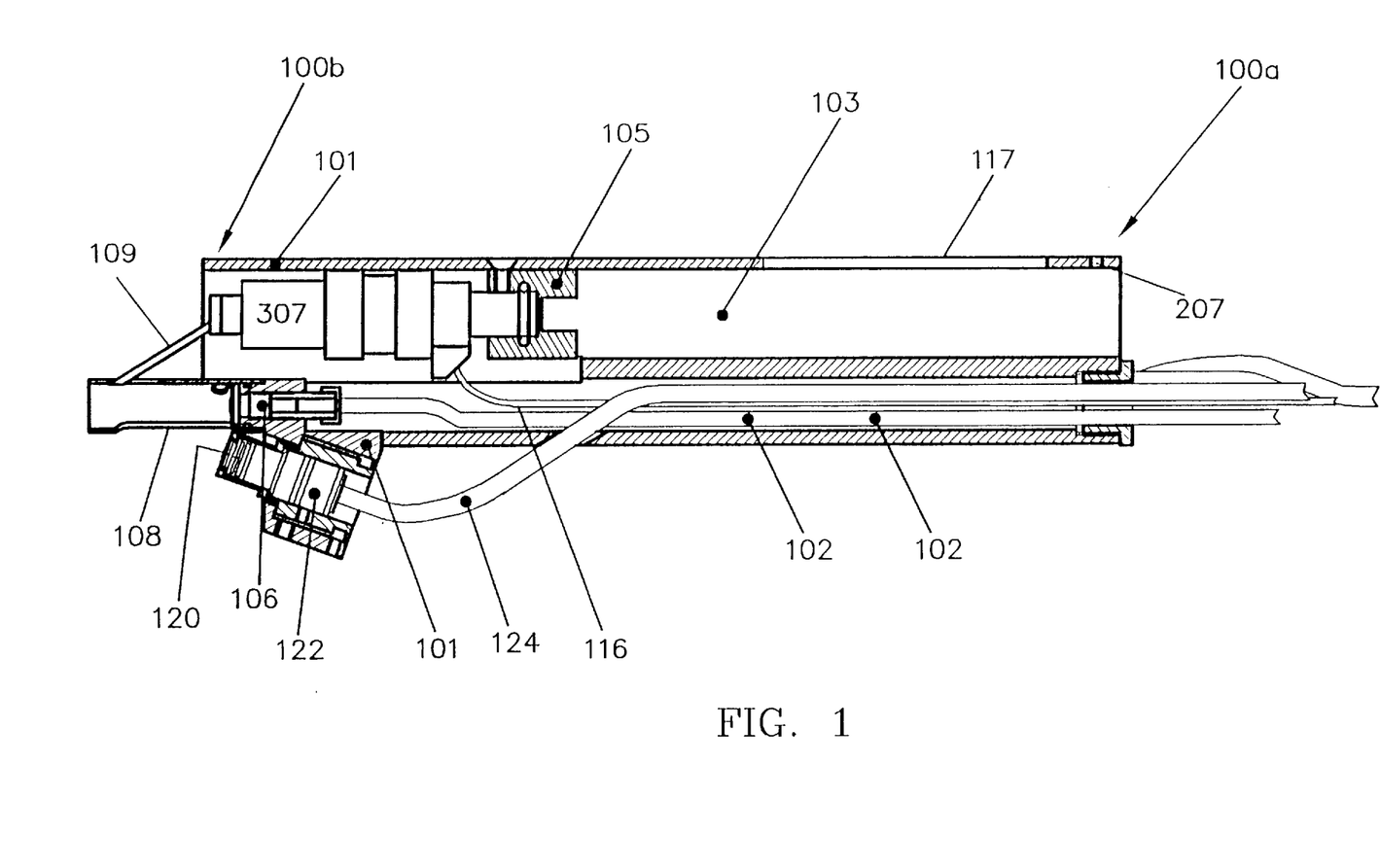
FIG. 1 is a representative section view of a preferred embodiment of a cooling handpiece with refillable coolant reservoir of the present invention.
Figure 2:
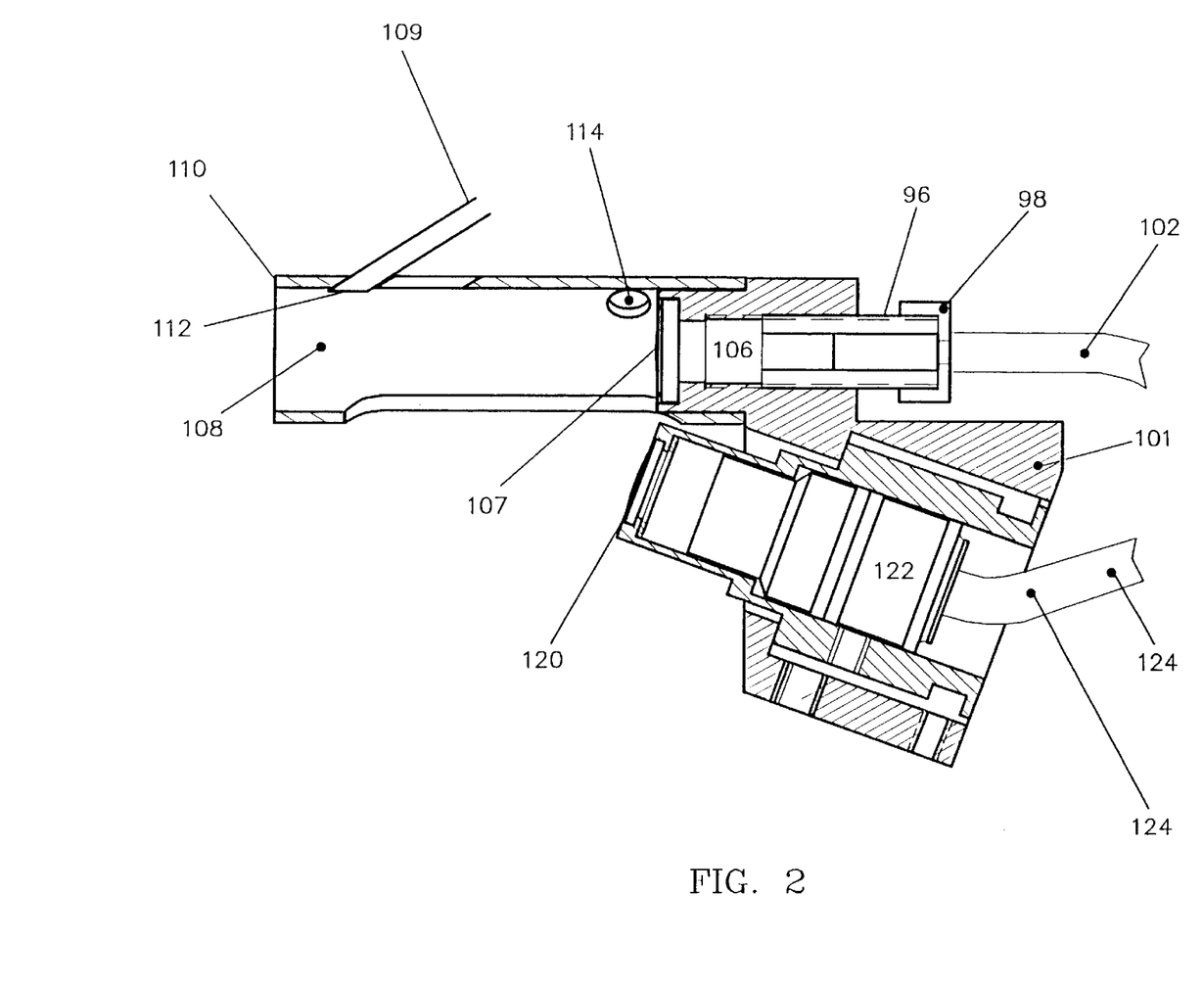
FIG. 2 is a representative detail section view of the distal end of a preferred embodiment of a cooling handpiece with removable coolant reservoir of the present invention.

FIG. 1 is a representative section view of a preferred embodiment of a cooling handpiece with refillable coolant reservoir of the present invention. FIG. 2 is a representative detail section view of the distal end of a preferred embodiment of a cooling handpiece with removable coolant reservoir of the present invention. The handpiece 100 has a housing 101 with a proximal end 100a and a distal end 100b.

A laser or other functional or interventional energy source (not shown) is connected to an energy delivery means 102. Energy delivery means 102 typically comprises a single optical fiber, e.g. 400 micron diameter, a fiber optic cable, a fiber bundle or other fiber optic laser delivery device. While the present invention may be fully operable and efficacious utilizing a CO2 laser, it will be understood that the present invention is especially suited for use with those energy sources capable of being transmitted conveniently via optical fibers. These include white light, infrared energy, Q-switched ruby lasers, flashlamp-pumped type pulsed dye lasers, Nd:YAG, Holmium-type and other solid-state lasers in use and known currently or in the future.

Moreover, the handpiece may optionally utilize any other operative energy source or functional device, including infrared or ultraviolet, x-ray or radio frequency delivery means, coherent or non-coherent energy, ultrasound delivery means, mechanical cutting tools, drilling apparatus, etc., or combination of the above. Applications which induce a thermal effect in the tissue can be controlled using the handpiece of the present invention, and applications which utilize tissue cooling in their performance are all included within the scope of this invention.

A distal end 104 of the energy delivery device 102 is fixed within the distal end 100b of the handpiece by SMA connector 98. The SMA connector is threaded onto a nipple 96 which itself is threaded into housing 101. An optional lens or other energy focusing device 106 is disposed adjacent the distal end 104 of the energy delivery device 102, and threaded nipple 96 allows for manual adjustment and precise orientation of distal end 104 of energy delivery device 102 and focusing means 106. It will be understood that a great variety of design factors must be considered and will be included in the scope of the present invention. Providing focusing means either integral with or separate from the laser or other energy delivery means allows flexibility in treatment or coverage, allows creation of different spot sizes and other parameter optimization depending upon the application, e.g. wrinkle removal, collagen shrinking, collagen stimulation or synthesis, blanching of port wine stains, photoablation in a cutting or tissue removal application, etc. It will be understood that in other preferred embodiments the focusing lens 106 is optionally located elsewhere within the apparatus 100, and in other preferred embodiments a plurality of focusing means are located at different positions within the apparatus 100.

A transparent delivery tube 108 is mounted adjacent the distal end 100b of the handpiece 100 in operative relationship with the distal end 104 of the energy delivery device 102 and the optional lens or other focusing device 106. Thus, laser or other energy which enters the delivery tube 108 radiates therefrom at distal end 110. The length of the delivery tube may vary depending upon the desired spot size, the need to provide an extending tip and the type of laser delivery means used. The focusing means is also adjustable in preferred embodiments. Typical laser delivery device delivery tubes such as those known as *Handpiece Extenders,* Part Nos. RD-1100 and RD-1200 made by Spectrum Medical Technologies, Inc. in Natick, Mass. are commercially available.

The delivery tube 108 is preferably transparent and tubular, but can have a plurality of different cross sectional geometries. A preferred embodiment is about 4-5 centimeters in length, but can be longer or shorter, depending upon desired spot size, etc. Adjacent the distal end 110 of the delivery tube 108 there is a coolant port 112 which directs coolant toward the distal end 110 and target tissue, as desired. The design of delivery tube 108 will prevent possible "fly-away" of ablated tissue, cells or blood, providing protection from cross contamination for other inhabitants and equipment in the operating room. The tube will also direct the fluid cryogen to specific areas conveniently. Waste of cryogen and loss of containment thereof as well as the risk for unintended contact with the cryogen is also minimized thereby.

An additional advantage of the delivery tube 108 of the present invention is to provide a means for marking the surface of the tissue which has been treated or visualized, etc. Small pressure marks, indentations, or other markings, dyes, etc. can be formed or released by the distal end 110 of the delivery tube 108. Thus, in the example of wrinkle removal using laser energy, the surface of skin which is irradiated and cooled using cryogen or other coolant bears no immediate visual indication of having just been treated, and the operator is thus aided by the visual indications made by the distal end 110 of the delivery tube 108.

Adjacent the proximal end 112 of the delivery tube 108, air vent 114 allows air or other fluid or gas to be flushed across outer surface 107 of lens means 106. In the absence of the vent 114 and flowing gas, other means may be used to prevent accumulation and consequential fogging or other distortion of focusing means 106 by condensation of water or other vapor on the outer surface 107 of focusing means 106. Such means could include means for heating the lens and preventing condensation of vapor thereon.

Providing a transparent delivery tube 108 also provides the physician or technician with an unobstructed view of the treatment in progress. Preferred embodiments have enhanced transmitting features, including anti-reflection coatings to protect the internal optical system and eliminate the potential for energy backlash, and perpendicular positioning means which reduce the risk of reflected light which could otherwise create a vision hazard in the operating room.

A thermal feedback system comprises a lens 120 for focusing a detected infrared output from the treated and/or cooled target tissue onto a thermal sensor 122. Such thermal sensor 122 can be any operative thermal sensor such as a thermopile, etc. A typical sensed output from cooled target tissue is radiation at about 10 microns, or more or less, and will be a function of the type of thermal sensor 122 selected. A feedback signal is transmitted via sensor output 124 to the central processing unit of the energy delivery device, such as an on-board controller for a laser system. As mentioned above, various control schemes, protocols and other methods are known to those skilled in the art and will additional and new ones will be apparent. The present invention is intended to provide a novel apparatus for effecting these protocols. Such protocol might call for initial steps including laser operation and controller tests, delivery means integrity and connection tests, and thermally sensing the status of the target tissue. During operation, the temperature of the target tissue can be sensed continuously or at discrete time points. Excessive precooling, simultaneous cooling and post-cooling of the target tissue can be avoided, thereby preventing tissue damage due to excessive cooling, and other thermal mediation of surface strata of the target tissue during thermal treatment of sub-surface strata, etc.

Figure 3:
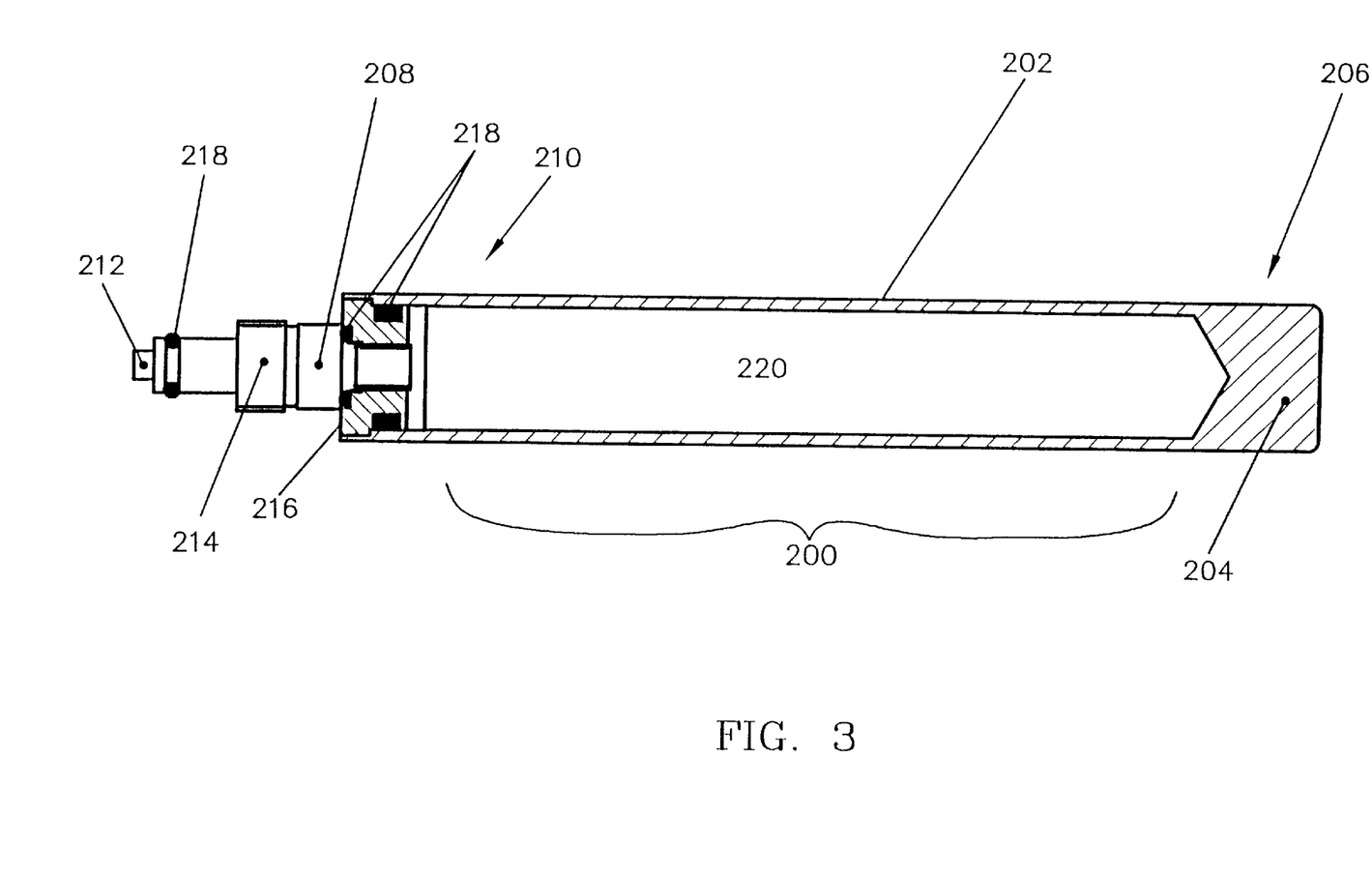
FIG. 3 is a representative section view of a preferred embodiment of a coolant reservoir of the present invention.

FIG. 3 is a representative section view of a preferred embodiment of a coolant reservoir 200 of the present invention. Reservoir 200 consists of a cylindrical tubular outer wall 202, an integrally formed sealed portion 204 at a proximal end 206 and a valve assembly 208 at a distal end 210. The proximal end 206 can also be capped or closed with a removable portion so as to allow filling from either end. The valve assembly 208 comprises a valve actuator 212 and male threaded portion 214, and is coupled to a plug portion 216 mounted within the distal end 210 of the reservoir 200. Sealing o-rings 218 are used between the tube 202 and the plug 216, between the plug 216 and the valve assembly 208, and adjacent the valve actuator 212. Reservoir chamber 220 contains a certain volume of cryogenic fluid or other coolant. In a preferred embodiment, the reservoir 200 consists of a tube 202 between about 0.25 and 1.0 inches in diameter, or narrower or wider, and between about 4.0 and 8.0 inches long, or shorter or longer, manufactured out of plastic, glass or other suitable material.

In preferred embodiments, the reservoir 200 can be either refillable or replaceable. In the refillable embodiment, suitable nozzle cap or other fill means is provided on the reservoir 200. In the replaceable embodiment, the reservoir is a disposable canister which can be purchased in advance and stocked at the hospital or clinic. A suitable attachment or mounting means is provided to conveniently, efficiently and safely remove an empty reservoir when empty and replace it with a full canister. The reservoirs have either threaded end fittings or bayonet-type locking means for providing a leak-proof, secure attachment between the reservoir 200 and rest of the handpiece 100. It will be apparent to those skilled in the art that the disposable and replaceable coolant reservoirs 200 can be manufactured with a wide range of variation in attachment means, volume, shape and materials, all of which are included in the scope of this invention.

In a preferred embodiment, the reservoir chamber 220 has a volume of between about 10 and 500 milliters, or more or less as may be desired or necessary for particular applications. Freon and liquid CO2 have been widely used cryogens and are well known in the field of cryosurgery. Another appropriate cryogen spray would be 1,1,1,2-tetrafluoroethane, $C_2H_2F_4$, an environmentally compatible, non-toxic, non-flammable freon substitute. Other cryogens, such as 134R (also a freon substitute), may also be used, and based upon this description will be apparent to those skilled in the art.

Figure 4:
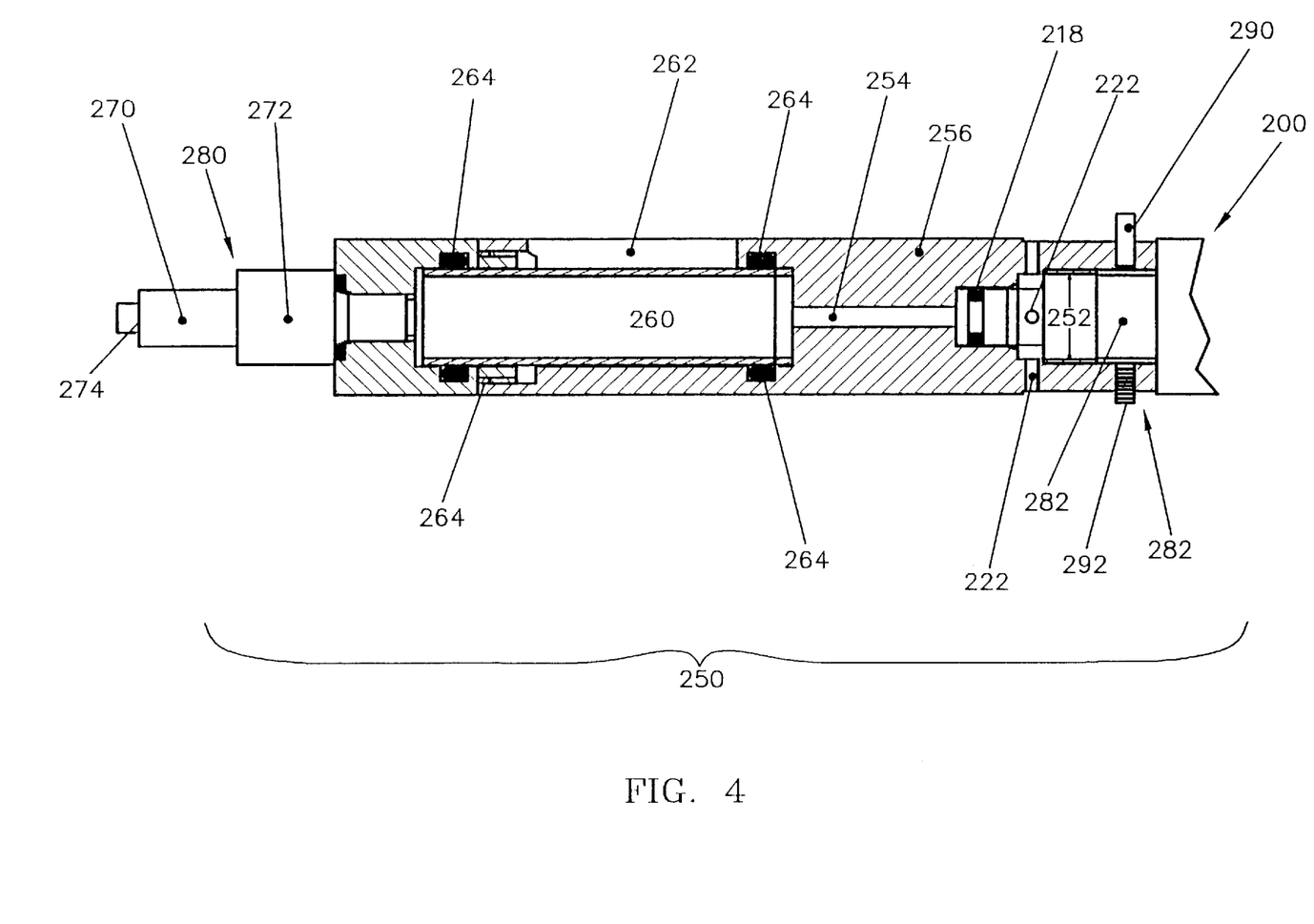
FIG. 4 is a representative section view of a preferred embodiment of a fluid level indicator accessory of the present invention.

FIG. 4 is a representative section view of a preferred embodiment of a fluid level indicator adapter 250 of the present invention. As shown, reservoir 200 threads into female threaded portion which results in valve assembly 208 opening and allowing coolant to flow from reservoir chamber 220 through valve assembly 208 and through coolant channel 254 in body 256 of adapter 250. Channel 254 empties into sight glass chamber 260 which is visible through window 262 in body 256 of the adapter 250 and through window 117 of handpiece housing 102. Additional sealing o-rings 264 are shown. At the distal end 280 of the adapter 250, optional valve assembly 270 comprising insert portion 272 and valve actuator 274 serves to seal the adapter at that end in the situation where the adapter 250 is removed from the handpiece 100 while a reservoir 200' containing coolant is coupled thereto. At the proximal end 282 of the adapter 250, adapter vent holes 222 allows venting of any coolant remaining in the sight glass chamber 260 during disassembly of the apparatus.

A safe, redundant, security locking system between the coolant reservoir 200 and adapter 250 comprises a threaded portion 252 and corresponding threaded portion on reservoir 200' and set screw 292. It will be understood that the reservoir 200 can be mounted onto the adapter 250 either before or after the adapter 250 is coupled to the handpiece 100. In either case, the adapter 250 slides into recess 103 in handpiece 100 such that insert portion 272 is disposed within receiving base 105, and bayonet pin 290 engages pin slot 207 at the proximal end 100a of the handpiece 100. It will be understood that the receiving recess 103 can be any operative mounting opening, slot, flange, area, pad, surface etc. Additionally, set screw 292 can be threaded through the proximal end 282 of the adapter 250 so as to prevent release of the reservoir 200 from the bayonet mount of the adapter 250.

Coolant is delivered from the reservoir 200 through controllable cryogen valve 307. Valve 307 can be a low-temperature solenoid-type valve which delivers spurts of cryogen as desired. Common automotive or other industrial liquid fuel injectors can also be used. Delivery of spurts between about 10 milliseconds and about 500 milliseconds in length are possible with various types of valves. Typically, the solenoid-type valve 307 is able to withstand pressures of up to about 80 to 100 PSI and temperatures as low as about −30 to −40 degrees Celsius.

After passing through the valve 307, the cryogen is directed through channel 109 and into the delivery tube 108 at channel port 112. Controller wires 116 will actuate the valve means, as desired, allowing cryogen to flow into the delivery tube 108. In a preferred embodiment, a spraying nozzle means is employed such that the cryogen is sprayed onto a preselected surface area in a predetermined pattern or at a predetermined flowrate, velocity, etc.

As described above, various dynamic cooling protocols, methods and systems are well known for use with thermally mediated treatment of biological tissue and other materials. Simultaneously or alternatingly, predetermined amounts of laser energy as well as cryogenic coolant can be delivered to the operating site precisely according to temperature and position sensors and on-board computing means associated with the laser source. Controllers based upon theoretically-derived or actually measured operating parameter data will allow the physician or technician to maintain a predetermined thermal gradient or temperature profile throughout certain preselected tissue. These control schemes will be possible with the apparatus of the present invention and particular or individual control schemes for specific applications will be apparent to those skilled in the art. A preferred embodiment of the present invention includes a timing circuit to control according to predetermined operating parameters time and rate of laser energy delivery, time and rate of cryogen delivery, sequencing and overlap of those events with ablation, cooling periods, etc.

Other preferred embodiments of the present invention comprise temperature sensors located at various positions, such as at a distal end of the delivery tube. The temperature sensor will sense the temperature of either the tip of the delivery tube, the skin upon which the laser energy and the coolant are directed, or both. Temperature probes and methods are well known in the art. Such temperature sensors operate in a variety of different ways, including black-body type radiation sensors, thermocouples, thermometers, etc. The temperature sensor provides information to a controller with feedback control of the laser, coolant delivery switch, etc.

A preferred embodiment of the present invention comprises a laser and/or cryogen interlock system. In the event the handpiece is held such that vapors in the reservoir are delivered before liquid, a substantial decrease in cooling effect is observable. Venting of cryogen fumes is very inefficient relative to the degree of cooling which can be achieved using liquid cryogen. Unless the surgeon is careful, during operation the handpiece can be manipulated in such a way as to tilt or turn the handpiece so that the liquid cryogen flows away from the solenoid or other flow valve. To prevent discharge of vapors, and sometimes more importantly, to prevent delivery of laser energy in the absence of sufficient coolant an interlock system is used. This system can be configured in a number of different ways, as will be apparent to those skilled in the art. Mercury switches to prevent switch actuation at certain orientations are widely used. Integrated circuits and other types of microprocessors or micro-devices are also available for such level control. Such a device ensures adequate orientation, such as a vertical position, of the handpiece prior to delivery of laser energy. Additionally, the interlock can be tied into a temperature sensor/control circuit. Such a circuit ensures a suitably low temperature at the skin surface or at a distal point on the valve or delivery tube prior to permitting delivery of laser energy. Another embodiment of the preferred embodiment measures fluid flow through the valve. Such apparatus prevents delivery of laser energy until and unless fluid cryogen is flowing at a predetermined minimum rate.

Figure 5:
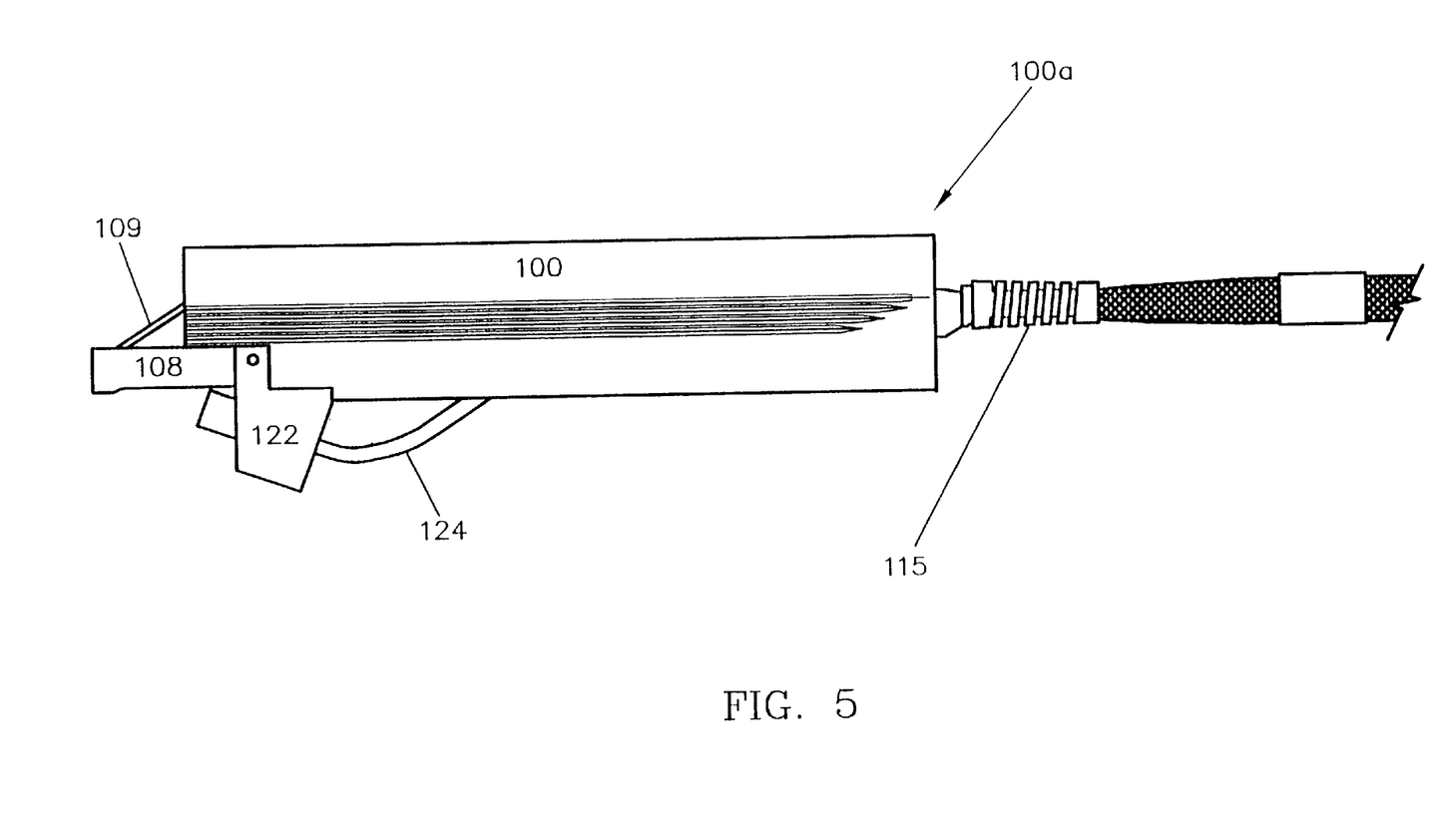
FIG. 5 is a representative perspective view of a preferred embodiment of a cooling handpiece with refillable coolant reservoir of the present invention.

FIG. 5 is a representative perspective view of a preferred embodiment of a cooling handpiece with refillable coolant reservoir of the present invention. At the proximal end 100a of the handpiece 100 there is a strain relief assembly 115 which encloses any or all of the following: the energy delivery means 102, the output 124 from thermal sensor 122, and controller lines 116 for actuating coolant flow.

Figure 6:
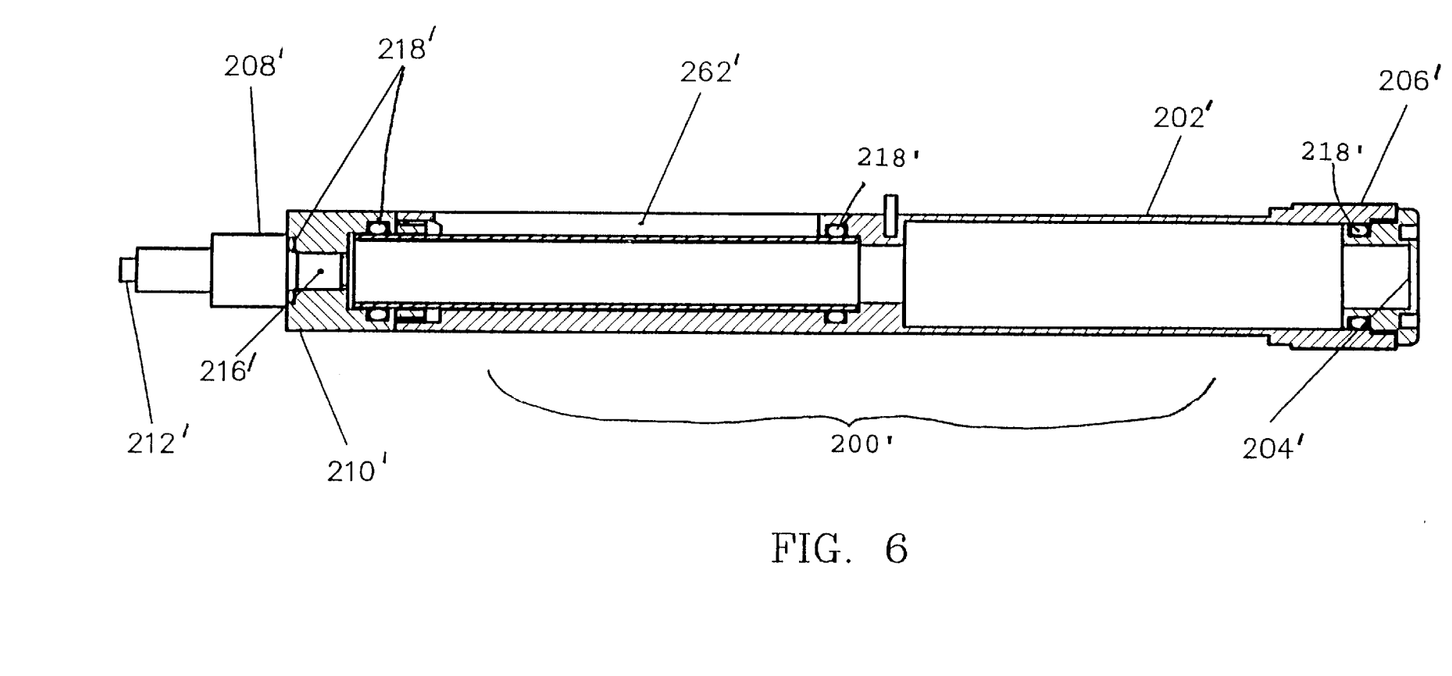
FIG. 6 is a representative section view of another preferred embodiment of a coolant reservoir of the present invention.

FIG. 6 is a representative section view of another preferred embodiment of a coolant reservoir 200' of the present invention. This reservoir 200' has a built-in sight glass 262' for determining remaining coolant volume. Reservoir 200' consists of a cylindrical tubular outer wall 202', an sealed portion 204' at a proximal end 206' and a valve assembly 208' at a distal end 210'. The proximal end 206' can also be capped or closed with a removable portion so as to allow filling from either end. The valve assembly 208' comprises a valve actuator 212' and is coupled to a plug portion 216' mounted within the distal end 210' of the reservoir 200'. Sealing o-rings 218' are used between the tube 202' and the plug 216', between the plug 216' and the valve assembly 208', and adjacent the valve actuator 212'. Remaining fluid volume can be determined by the operator or technician by looking through the sight glass window 262' and through window 117 of handpiece body 102.

Figure 7:
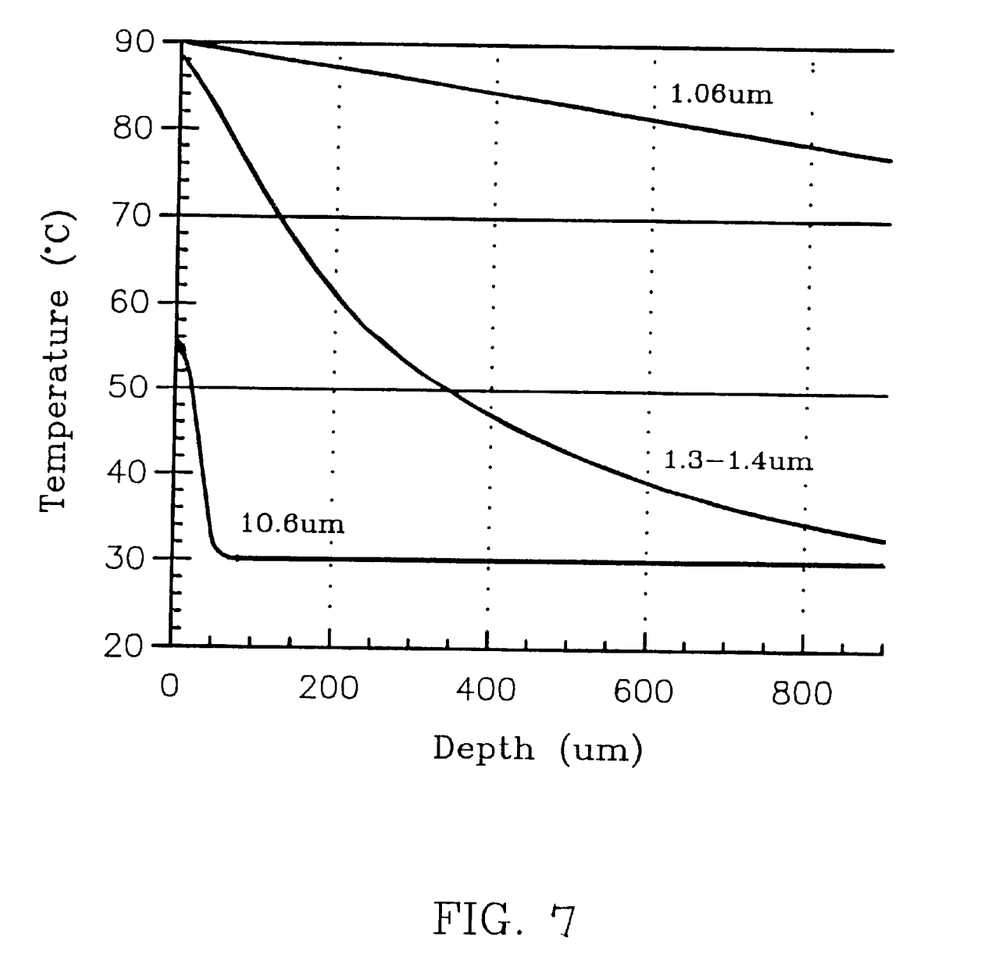
FIG. 7 is a graph demonstrating the temperature gradient through a portion of the skin without precooling as a function of both the wavelength of incident laser energy and the depth of laser radiation penetration.

FIG. 7 is a graph demonstrating the experimentally obtained temperature gradient through a portion of the skin without precooling as a function of both the wavelength of incident laser energy and the depth of laser radiation penetration. The graph demonstrates a change in temperature ($\Delta T$) of about 60 degrees Celsius and all curves are shown for the time point 1 millisecond following exposure to the laser energy. The graph shows three lines corresponding to laser wavelengths of 10.6 microns, 1.3–1.4 microns and 1.06 microns.

Figure 8:
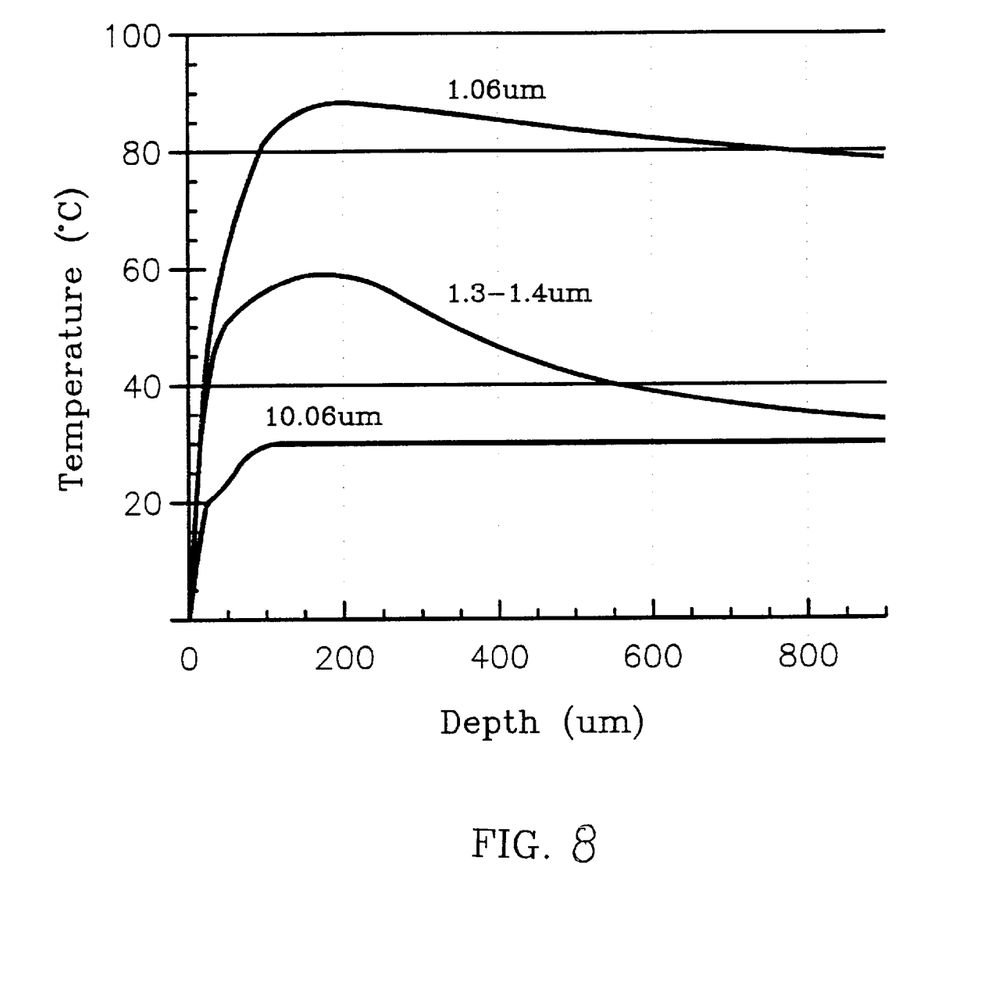
FIG. 8 is a graph demonstrating the temperature gradient through a portion of the skin with precooling as a function of both the wavelength of incident laser energy and the depth of laser radiation penetration.

FIG. 8 is a graph demonstrating the temperature gradient through a portion of the skin with precooling as a function of both the wavelength of incident laser energy and the depth of laser radiation penetration. The graph demonstrates a change in temperature ($\Delta T$) of about 60 degrees Celsius. In these experiments, precooling of the skin surface tissue for a period of 20 milliseconds was conducted immediately prior to exposure to laser energy. All curves are shown for a time point 1 millisecond following exposure to the laser energy. The graph shows three lines corresponding to laser wavelengths of 10.6 microns, 1.3–1.4 microns and 1.06 microns. It will be understood that the parameters of time, cooling and exposure to laser energy may be varied manually or automatically, as desired.

Studies have shown that irradiating tissue with a midinfrared laser source through a surface thermal absorption element or heat sink permits an optimum thermal profile within the target tissue with near physiologic temperature at the surface of the irradiated surface thus minimizing surface thermal damage. In the case of desired thermal collagen shrinkage, this is clearly the desired condition. Others have shown that attenuating the surface temperature before laser irradiation and therefore creating a boundary layer on the skin surface can result in selective cooling of the target tissue thus preserving the normal overlying epidermis.

During a typical dynamic cooling process, the surface of the skin is pre-cooled to as low as 0 degrees Celsius or lower, at a rate fast enough to cool the surface only but not dissipate heat from below about 400–500 microns below the surface. In a preferred embodiment, during the cooling step the target tissue remains at body temperature and is not cooled at all.

For example, in laser-induced shrinkage of collagen tissue, by applying cooling to the surface of the skin for a short period of time, typically between about 5 and 100 milliseconds, and then delivering laser energy, the surface is initially cooled but the target tissue never is. Generally, the surface layer of skin is rapidly cooled. A high rate of cooling will prevent proximal hypothermia and will also tend to have a numbing, anesthetic or analgesic effect. Therefore, upon delivery of laser energy onto the surface and therethrough, the target tissue will be raised to the optimal thermal shrinkage temperature and generally not any higher, in an adequately rapid process.

In a preferred embodiment of the method of the present invention, cooling and heating are performed in a predetermined timing sequence, optionally with the use of timer circuits and/or other controller means.

With respect to studies performed removing sub-dermal skin lesions, such as port wine stains and other red or brown marks, an optimum cooling strategy might be one that uses a short spurt of cryogen (e.g., 5–20 ms) to reduce the local temperature in the pigmented epidermis, while minimizing attenuation of the laser light by the boundary layer, followed by post-irradiation cooling spurt that provides a heat sink for dissipation of the epidermal heat generated by melanin absorption. The present invention includes and encompasses all of the above.

Unless defined otherwise, all technical and scientific terms used herein have the same meaning as commonly understood by one of ordinary skill in the art to which this invention belongs. Although any methods and materials similar or equivalent to those described can be used in the practice or testing of the present invention, the preferred methods and materials are now described. All publications and patent documents referenced in this application are incorporated herein by reference.

The Nd:YAG, Nd:YAP and Nd:YALO-type lasers are such sources of coherent energy. This wavelength of 1.3–1.4 microns is absorbed relatively well by water, and as a result is attractive for tissue interaction. It is also easily transmitted through a fiber optic delivery system as opposed to the rigid articulated arm required for the $CO_2$ laser. Very precise methods of controlling laser systems and optically filtering produced light currently exist. By selecting the appropriate combination of resonance optics and/or anti-reflection coatings, wavelengths in the range of 1.3–1.4 microns and even 1.32–1.34 microns can be produced.

Light transport in skin and other tissues is dominated by primary and secondary scattering events, rather than by optical absorption alone. Lask G, et al. Nonablative Laser Treatment of Facial Rhytides; SPIE Proc. 1997; 2970 :xxx.

The concept of an "effective attenuation coefficient" $\mu_{eff}$ (in an exponential attenuation relation similar to Beer's law for absorption alone) has been used traditionally to approximate the light fluence $\phi$ (units: J/cm$^2$) within a tissue in which scattering is important:

$$\phi(z) = A \exp(\mu_{eff} z) \quad [1]$$

$$\mu_{eff} = \{3\, \mu_a [\mu_a + \mu_s(1-g)]\}^{1/2} \quad [2]$$

where A is a constant, z is the depth (units: cm) within the tissue, $\mu_a$ is the absorption coefficient (units: cm$^{-1}$), $\mu_s$ is the scattering coefficient (units: cm$^{-1}$), and g is the scattering anisotropy (units: dimensionless). Welch A. J., van Gemert M. J. C. (editors), Introduction to medical applications: Optical-Thermal Response of Laser-Irradiated Tissue. (Plenum Press, New York, 1995), pp. 609–618.

Light fluence $\phi$ is the energy (units: J) passing through a cross-sectional area (units: cm$^2$) from all directions. It differs from the radiant exposure F (units: J/cm$^2$) which we use in describing treatment parameters since F is the energy density directed onto the tissue surface from the light source. The fluence $\phi$ can be much larger than the radiant exposure F due to multiple scattering events—see FIG. 1 of Welch et al. When the tissue is highly scattering, on the average many photon scattering events occur before the photon is ultimately absorbed.

If the real light fluence distribution were represented by Equation [1], the "effective optical absorption" as a function of depth z would mimic this exponential function and the "effective optical absorption coefficient" would be given by Equation [2]. However, the real light fluence distribution is more complicated than Equation [1] indicates and is best represented by a Monte Carlo modeling calculation which includes the effects of initial light distribution striking the tissue (e.g., collimated light at normal incidence, diffuse light at non-normal incidence, etc.), the changes of index of refraction at the air/tissue interface (and at any other interfaces within the tissue), absorption and scattering events within the tissue, and remittance from the tissue (by reflection at the air/tissue interface and by backscattering from within the tissue). Jacques S L, Wang L. Monte Carlo modeling of light transport in tissues: Optical-Thermal Response of Laser-Irradiated Tissue. (Plenum Press, New York, 1995), pp. 73–100.

For the purposes of the present invention, it will be understood that the term "non-homogeneous collagen" will refer to that collagen typically found in human or other animal skin, as described in the preceding paragraph. Non-homogeneous collagen is also anisotropic by nature, in that it does not exhibit identical properties (such as light transmission, birefringence, conductivity of heat or electricity) when measured along axes in different directions. It is well known that skin tissue is composed of such non-homogeneous collagen, as compared to other transparent, isotropic and homogeneous collagen-containing tissue, such as that of the cornea.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true purview, spirit and scope of the invention.

We claim:

1. A cooling handpiece comprising:

a main body portion having a proximal end and a distal end;

controllable energy delivery means for controllably delivering energy from the distal end of the main body portion to target tissue;

a reservoir receiving recess integral with the main body portion the reservoir receiving recess defined by a tubular receiving portion, receiving base and releasable mounting means;

removable coolant reservoir shaped to operatively fit within the reservoir receiving recess of the handpiece and having contained therein coolant fluid, the coolant reservoir releasably mountable releasable mounting means on the handpiece within the reservoir receiving recess; and a controllable valve for controllably delivering a portion of the coolant fluid to the target tissue.

2. The handpiece of claim 1 further comprising a delivery tube for directing the energy from the energy delivery means as well as the coolant fluid onto the target tissue, the delivery tube having a proximal end and a distal end.

3. The handpiece of claim 1 in which the reservoir comprises a tubular portion with an at least partially transparent sidewall for providing visual indication of the volume of coolant fluid remainiug in the reservoir.

4. The handpiece of claim 1 in which the valve means comprises a controllable solenoid valve.

5. The handpiece of claim 1 further comprising means for focusing the energy being delivered to the target tissue.

6. The handpiece of claim 1 in which the reservoir is refillable.

7. The handpiece of claim 1 in which the releasable mounting means comprises matching threaded end fittings on both the reservoir and the main body portion.

8. The handpiece of claim 1 in which the releasable mounting means is a locking, bayonet-type mounting means comprising a locking pin and mating slot.

9. The handpiece of claim 1 further comprising a thermal sensor and feedback control means for preventing undesirable delivery of energy to the target tissue.

10. The handpiece of claim 1 further comprising an energy delivery interlock means for preventing undesirable delivery of energy to the target tissue.

11. The handpiece of claim 10 in which the energy delivery interlock means includes a fluid level switch.

12. The handpiece of claim 10 in which the energy delivery interlock means includes a thermal sensor.

13. The handpiece of claim 10 in which the energy delivery interlock means includes a fluid flow sensor.

14. A cooling handpiece comprising:

a main body portion having a proximal end and a distal end, the main body portion adapted for directing energy from a controllable energy delivery device to target tissue, the main body portion having a reservoir receiving recess integral with the main body portion, the reservoir receiving recess defined by a tubular receiving portion, receiving base and releasable mounting means for receiving a removable coolant reservoir, the reservoir releasably mountable via releasable mounting means within the reservoir receiving recess of the main body portion; and a controllable valve for controlled delivery of coolant from the reservoir to the target tissue.

15. The handpiece of claim 14 further comprising an energy delivery device having a distal end and a proximal end, the device for receiving energy at its proximal end and transmitting the energy to its distal end for delivery to the target tissue.

16. The handpiece of claim 14 further comprising a coolant reservoir.

17. The handpiece of claim 14 further comprising a thermal sensor, the thermal sensor mounted to the handpiece to sense the temperature of the target tissue.

18. The handpiece of claim 14 further comprising a delivery tube for positioning the handpiece adjacent target tissue and for directing energy from an energy delivery means as well as coolant onto the target tissue, the delivery tube having a proximal end and a distal end.

19. The handpiece of claim 16 in which the reservoir comprises a tubular portion with an at least partially transparent sidewall for providing visual indication of the volume of coolant remaining in the reservoir.

20. The handpiece of claim 14 further comprising an adapter coupling between the coolant reservoir and the main body portion of the handpiece.

21. The handpiece of claim 20 in which the adapter further comprises a coolant chamber and a sight glass for providing a visual indication of remaining coolant.

22. The handpiece of claim 14 in which the controllable valve comprises a controllable solenoid valve.

23. The handpiece of claim 14 further comprising means for focusing the energy being delivered to the target tissue.

24. The handpiece of claim 16 in which the reservoir is refillable.

25. The handpiece of claim 14 in which the releasable mounting means on the reservoir comprises a set of helical threads and the handpiece further comprises an operative set of mating helical threads, the two sets of helical threads operative to releasably couple the reservoir to the handpiece.

26. The handpiece of claim 14 in which the releasable mounting means on the reservoir comprises a bayonet-type mounting locking pin and the handpiece further comprises an operatively positioned mating slot for the locking pin.

27. The handpiece of claim 14 further comprising a thermal sensor and feedback control means for preventing undesirable delivery of energy to the target tissue.

28. The handpiece of claim 14 further comprising an energy delivery interlock means for preventing undesirable delivery of energy to the target tissue.

29. The handpiece of claim 28 in which the energy delivery interlock means includes a coolant level switch.

30. The handpiece of claim 28 in which the energy delivery interlock means includes a thermal sensor.

31. The handpiece of claim 28 in which the energy delivery interlock means includes a coolant flow sensor.

32. A method of performing a thermally mediated procedure using a cooling handpiece with (1) a main body portion having a proximal end and a distal end, the main body portion adapted for directing energy from a controllable energy delivery device to target tissue, the main body portion having a reservoir receiving recess integral with the main body portion, the reservoir receiving recess defined by a tubular receiving portion, receiving base and releasable mounting means for receiving a removable coolant reservoir the reservoir releasably mountable via releasable mounting means within the reservoir receiving recess of the main body portion of the handpiece, and (2) a controllable valve for controllable delivery of a portion of the coolant to the target tissue, the method comprising the following steps:

(a) operatively coupling a coolant reservoir containing coolant to the handpiece;

(b) controllably delivering a coolant to the target tissue;

(c) controllably delivering energy to the target tissue;

(d) interrupting delivery of energy when the reservoir is empty or is nearly empty; and (e) removing empty or nearly empty reservoir.

33. The method of claim 32 further comprising the following step:

(f) refilling tie reservoir with coolant.

34. The method of claim 32 further comprising the following step:

(g) visually monitoring the volume of coolant fluid remaining in the handpiece.

35. A handpiece for controllable delivery of functional energy and surface coolant to target tissue comprising:

a main body portion having a proximal end and a distal end, the main body portion adapted for receiving functional energy and for directing functional energy from the distal end to target tissue, the main body portion having a reservoir receiving recess integral with the main body portion, the reservoir receiving recess defined by a tubular receiving portion, receiving base and releasable mounting means for receiving a removable coolant reservoir, the reservoir releasably mountable via releasable mounting means within the reservoir receiving recess of the main body portion of the handpiece; and a controllable valve disposed between the attachment means and the distal end for controlled delivery of a portion of the coolant to the target tissue.

36. The handpiece of claim 35 further comprising a reservoir containing coolant.

37. A method for treating skin using a handpiece for controlled delivery of interventional energy and surface coolant to target tissue, the handpiece having a main body portion with a proximal end and a distal end, the main body portion adapted for receiving interventional energy and for transmitting the interventional energy from the distal end to target tissue, the main body portion having a reservoir receiving recess integral with the main body portion, the reservoir receiving recess defined by a tubular receiving portion, receiving base and releasable mounting means for receiving a removable coolant reservoir, the reservoir releasably mountable via releasable mounting means within the reservoir receiving recess of the main body portion of the handpiece, the handpiece also having a controllable valve for controlled delivery of a portion of the coolant to the target tissue, the method comprising the steps of placing the distal end of the handpiece adjacent the target tissue, delivering coolant from the distal end of the handpiece to the surface of the target tissue, and transmitting interventional energy from the distal end of the handpiece to the target tissue.

38. The method of claim 37 in which the handpiece is adapted to receive interventional energy having a wavelength between about 1 micron and about 12 microns and in which the step of transmitting interventional energy includes transmitting the interventional energy having a wavelength between about 1 and about 12 microns.

39. The method of claim 37 in which the handpiece is adapted to receive interventional energy having a wavelength between about 1.3 micron and about 1.4 microns and in which the step of transmitting interventional energy includes transmitting the interventional energy having a wavelength between about 1.3 and about 1.4 microns.

40. The method of claim 37 in which the handpiece is adapted to receive laser energy and in which the step of transmitting interventional energy includes transmitting the laser energy.

41. The method of claim 37 in which the handpiece is adapted to receive non-coherent interventional energy and in which the step of transmitting interventional energy includes transmitting the non-coherent interventional energy.

42. The method of claim 37 in which the skin treatment includes wrinkle removal.

43. A method for treating tissue using a handpiece adapted for receiving and transmitting electromagnetic energy, the handpiece having a reservoir receiving recess integral with the main body portion, the reservoir receiving recess defined by a tubular receiving portion, receiving base and releasable mounting means for receiving a removable coolant reservoir the reservoir, releasably mountable via releasable mounting means within the reservoir receiving recess of the main body portion of the handpiece, the handpiece also having a controllable valve for controlled delivery of coolant to the target tissue, the method comprising the following steps: (1) delivering coolant from the handpiece to the surface of the target tissue, and (2) transmitting electromagnetic energy from the handpiece to the target tissue.

44. The method of claim 43 further including the following step: (3) optically detecting the remaining volume of coolant remaining in the reservoir.

* * * * *